US011135181B2

(12) United States Patent
Vitetta et al.

(10) Patent No.: US 11,135,181 B2
(45) Date of Patent: Oct. 5, 2021

(54) TREATMENT FOR DEPRESSION AND DEPRESSIVE DISORDERS

(71) Applicant: Medlab IP Pty Ltd, Alexandria (AU)

(72) Inventors: Luis Vitetta, Varsity Lakes (AU); Samantha Maree Coulson, Fig Tree Pocket (AU); Sean Hall, Sydney (AU)

(73) Assignee: Medlab IP Pty Ltd, Alexandria (AU)

( * ) Notice: Subject to any disclaimer, the term of this patent is extended or adjusted under 35 U.S.C. 154(b) by 578 days.

(21) Appl. No.: 15/523,271

(22) PCT Filed: Oct. 28, 2015

(86) PCT No.: PCT/AU2015/050673
§ 371 (c)(1),
(2) Date: Apr. 28, 2017

(87) PCT Pub. No.: WO2016/065419
PCT Pub. Date: May 6, 2016

(65) Prior Publication Data
US 2017/0312232 A1 Nov. 2, 2017

(30) Foreign Application Priority Data

Oct. 28, 2014 (AU) .............................. 2014904306

(51) Int. Cl.
| A61K 31/513 | (2006.01) |
| A61K 35/741 | (2015.01) |
| A61K 35/744 | (2015.01) |
| A61K 35/745 | (2015.01) |
| A61K 35/747 | (2015.01) |
| A61K 31/122 | (2006.01) |
| A23L 33/10 | (2016.01) |
| A23L 33/135 | (2016.01) |
| A61K 31/7076 | (2006.01) |
| A61K 36/06 | (2006.01) |
| A23L 33/175 | (2016.01) |
| A61K 9/48 | (2006.01) |
| A23L 33/15 | (2016.01) |
| A23L 33/00 | (2016.01) |
| A23L 33/16 | (2016.01) |
| A23L 2/52 | (2006.01) |
| A61K 9/00 | (2006.01) |

(52) U.S. Cl.
CPC .............. *A61K 31/122* (2013.01); *A23L 2/52* (2013.01); *A23L 33/10* (2016.08); *A23L 33/135* (2016.08); *A23L 33/15* (2016.08); *A23L 33/16* (2016.08); *A23L 33/175* (2016.08); *A23L 33/30* (2016.08); *A61K 9/0053* (2013.01); *A61K 9/4858* (2013.01); *A61K 31/513* (2013.01); *A61K 31/7076* (2013.01); *A61K 35/741* (2013.01); *A61K 35/744* (2013.01); *A61K 35/745* (2013.01); *A61K 35/747* (2013.01); *A61K 36/06* (2013.01); *A23V 2002/00* (2013.01)

(58) Field of Classification Search
None
See application file for complete search history.

(56) References Cited

U.S. PATENT DOCUMENTS

| 6,080,401 A | 6/2000 | Reddy et al. | |
| 6,541,027 B1 | 4/2003 | Antoine et al. | |
| 2003/0144244 A1* | 7/2003 | Hebert ................. | A61K 9/0014 514/45 |
| 2011/0020443 A1* | 1/2011 | Liu ....................... | A61K 31/191 424/464 |
| 2011/0152309 A1 | 6/2011 | Beppu et al. | |
| 2013/0064803 A1 | 3/2013 | Naidu et al. | |
| 2013/0344045 A1* | 12/2013 | Faure ................... | A61K 35/747 424/93.45 |

FOREIGN PATENT DOCUMENTS

| EP | 1177794 A2 | 2/2002 |
| EP | 2 085 377 A1 | 8/2009 |
| JP | 2004-059488 A | 2/2004 |
| WO | 01/85178 A1 | 11/2001 |
| WO | 03/066041 A1 | 8/2003 |
| WO | 2004/098622 A2 | 11/2004 |
| WO | 2009/069291 A1 | 6/2009 |
| WO | 2011/020780 A1 | 2/2011 |
| WO | 2012/080789 A1 | 6/2012 |

OTHER PUBLICATIONS

Ait-Belgnaoui et al., "Probiotic gut effect prevents the chronic psychological stress-induced brain activity abnormality in mice," *Neurogastroenterology & Motility* 26:510-520, 2014.
Bambling et al., "S-adenosylmethionine (SAMe) and Magnesium Orotate as adjunctives to SSRIs in sub-optimal treatment response of depression in adults: A pilot study," *Advances in Integrative Medicine* 2:56-62, 2015.
Desbonnet et al., "The probiotic *Bifidobacteria infantis*: An assessment of potential antidepressant properties in the rat," *Journal of Psychiatric Research* 43:164-174, 2009.
Luo et al., "Ingestion of *Lactobacillus* strain reduces anxiety and improves cognitive function in the hyperammonemia rat," *Science China Life Sciences* 57(3):327-335, 2014.
Karkishchenko et al., "Anxiolytic Effect of Potassium Orotate," *Farmak Toksik* 46:68-71, 1983 (+English abstract).
Lakhan et al., "Nutritional therapies for mental disorders," *Nutrition Journal* 7(2), 8 pages, 2008.
Lydiard et al., "Irritable Bowel Syndrome, Anxiety, and Depression: What Are the Links?" *J Clin Psychiatry* 62(Supp 8):38-45, 2001.
Messaoudi et al., "Assessment of psychotropic-like properties of a probiotic formulation (*Lactobacillus helveticus* R0052 and *Bifidobacterium longum* R0175) in rats and human subjects," *British Journal of Nutrition* 105:755-764, 2011.

(Continued)

*Primary Examiner* — Robert J Yamasaki
*Assistant Examiner* — Charles Zoltan Constantine
(74) *Attorney, Agent, or Firm* — Seed IP Law Group LLP

(57) ABSTRACT

Provided herein are methods and compositions for use in the treatment of depression, anxiety or a depressive or anxiety-related disorder. Embodiments describe the administration of orotic acid or a salt thereof, or the administration of one or more probiotic microorganisms, or administration of a combination of orotic acid or a salt thereof and one or more probiotic microorganisms.

18 Claims, 1 Drawing Sheet

(56) References Cited

OTHER PUBLICATIONS

Steenburgen et al., "A randomized controlled trial to test the effect of multispecies probiotics on cognitive reactivity to sad mood," *Brain, Behavior and Immunity* 48:258-264, 2015.

Köhler et al., "Effects of BCH 325 (Pro-D-Phe-Pro-Gly) on Open Field Behavior After Chronic Stress Procedure," *Peptides* 13:141-144, 1992.

"Orotates and the mineral transporters of Dr. Nieper," The Delano Report on Enhancement for Bodies and Minds, URL: www.delano.com/blog/?tag=orotates, 2009, downloaded Oct. 29, 2020, 14 pages.

\* cited by examiner

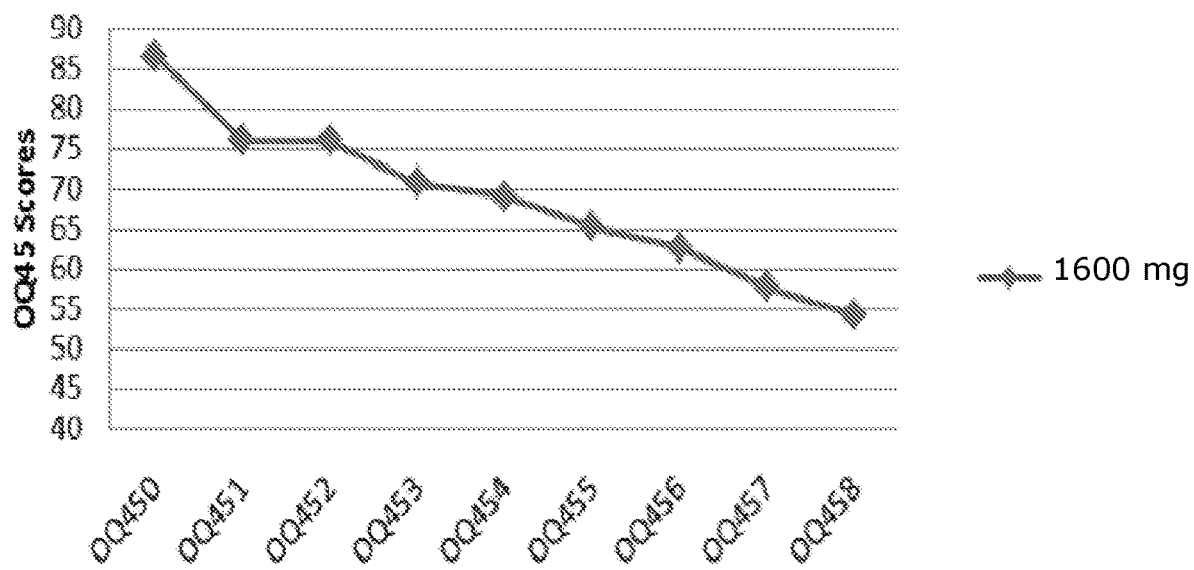

TREATMENT FOR DEPRESSION AND DEPRESSIVE DISORDERS

FIELD OF THE ART

The present disclosure relates generally to compositions and methods for the treatment of depression, anxiety and related disorders.

BACKGROUND

Depression is a highly prevalent mental health illness facing the health care system, with the burden of care second only to heart disease. Lifetime prevalence rates for depression in the Australian community have been estimated at 25% for females and 12% for males. The prevalence of depression and related disorders such as anxiety, and the impact such disorders have in society, is increasingly being realised. Major depressive disorder (or clinical depression) is thought to afflict anywhere from 10 to 20% of the population and is generally accepted as being a major contributing factor of most suicides. The World Health Organization ranks major depressive disorder as the fourth leading cause of disability worldwide and projects that by 2020 it will be the second leading cause.

Clinical depression is typically characterised by feelings of intense sadness and despair, mental slowing and loss of concentration, pessimistic worry, agitation, and self-deprecation. Physical changes also often occur, including insomnia or hypersomnia, anorexia and weight loss (or sometimes overeating), decreased energy and libido, and disruption of normal circadian rhythms of activity, body temperature, and many endocrine functions. Anxiety and depression are intertwined, anxiety in many individuals being a precursor to depression or a depressive disorder. Anti-depressant medications are often prescribed for sufferers of anxiety. The existence and prevalence of mixed anxiety-depressive disorder is now recognised by the World Health Organisation.

Depression and anxiety affect social functioning and productivity, including workplace productivity, and increases the risk of suicide and other chronic diseases such as cardiovascular disease, stroke, diabetes and obesity.

Anti-depressants typically prescribed include tricyclic antidepressants, tetracyclic antidepressants, selective serotonin reuptake inhibitors (SSRIs), and selective serotonin and/or noradrenaline reuptake inhibitors (SNRIs). While often helpful, these drugs are limited in their efficacy by their innate toxicity as well as a significant tendency to unpleasant and potentially dangerous side effects, such as nausea, sexual dysfunction, cognitive slowing, emotional dulling, lethargy, addiction and sleep disturbances, as well as potentially damaging interactions with other medications. There are also reports that some anti-depressant medication can exacerbate the tendency towards suicide or suicidal thoughts.

Antidepressant medication treatment assists with acute episodes; however, its efficacy is relatively poor for complicated chronic depressive illness. One third of people treated for depression relapse within a year, and those suffering two episodes have a 90% chance of suffering a third, with 40% relapsing within 15 weeks. These patients are considered resistant to current pharmacological treatments.

Resistant depression often presents with a variety of comorbid health problems such as gastro-intestinal, endocrine, and lipid disorders and gastrointestinal dysbiosis which imply complex physiological and gut pro-inflammatory mechanisms may be at work in terms of disease development and response to treatment.

Despite the clearly devastating effects of depression and anxiety it is thought that more than half of all sufferers either do not seek medical treatment or fail to take appropriate prescribed or recommended medication. In addition to the social stigma attached to depression and anxiety, a significant factor in this lack of compliance is the detrimental side effects of existing options for anti-depressant medication.

There remains a need for the development of improved efficacious therapeutic options for the treatment of depression and related disorders.

SUMMARY OF THE DISCLOSURE

In a first aspect the present disclosure provides a method for treating, preventing or ameliorating at least one symptom of depression, anxiety or a depressive or anxiety-related disorder, comprising administering to a subject in need thereof an effective dose of orotic acid or a salt thereof.

The orotic acid salt may comprise, for example, one or more of magnesium orotate, creatinine orotate, carnitine orotate, sodium orotate, calcium orotate, zinc orotate, chromium orotate, potassium orotate, copper orotate, iron orotate, manganese orotate, or choline orotate. In an exemplary embodiment the orotic acid salt is magnesium orotate, creatinine orotate or carnitine orotate. In specific embodiments of the present disclosure the orotic acid salt is not lithium orotate.

In an exemplary embodiment the orotic acid salt comprises magnesium orotate.

In an exemplary embodiment the orotic acid salt comprises magnesium orotate and the effective dose of magnesium orotate is about 800 mg per day or more. The effective dose may of magnesium orotate may be about 1600 mg per day.

In an embodiment the orotic acid or salt thereof is administered orally. The orotic acid or salt thereof may be, for example, in the form of a beverage, food, beverage or food supplement or in unit dosage form. The unit dosage form may be a capsule.

In exemplary embodiments the orotic acid or a salt thereof may be administered in combination with at least one additional agent selected from:

(i) one or more probiotic microorganisms;

(ii) coenzyme Q10 (optionally a reduced or oxidized form thereof); and/or (iii) SAMe or a salt thereof.

The orotic acid or salt thereof and at least one additional agent may be administered as a single composition or formulation, or may be administered as two or more separate compositions or formulations. Where separate compositions or formulations are administered, such administration may be simultaneous or sequential.

In specific embodiments, at least one of the components administered to the subject is administered orally.

The one or more probiotic microorganisms may comprise at least one *Lactobacillus* species, at least one *Lactococcus* species, at least one *Bifidobacterium* species, at least one *Streptococcus* species and/or at least one yeast.

The one or more probiotic microorganisms may be selected from, for example, *Lactobacillus rhamnosus*, *Lactobacillus plantarum*, *Lactobacillus bulgaricus*, *Lactobacillus gasseri*, *Lactobacillus reuteri*, *Lactobacillus paracasei*, *Lactobacillus casei*, *Lactobacillus acidophilus*, *Lactobacillus fermentum*, *Lactobacillus salvarius*, *Lactococcus lactis*, *Streptococcus thermophilus*, *Bifidobacterium breve*, *Bifido-* bacterium bifidum, *Bifidobacterium animalis* subsp. *lactis*, *Bifidobacterium animalis* subsp. *animalis*, *Bifidobacterium infantis*, *Bifidobacterium longum*, *Bifidobacterium pseudocatenulatum*, *Saccharomyces boulardii* or *Saccharomyces cerevisiae*.

In exemplary embodiments the *Lactobacillus* species may be selected from *L. acidophilus*, *L. bulgaricus*, *L. paracasei*, *L. gasseri* and *L. rhamnosus*; the *Lactococcus* species may be *L. lactis*; the *Bifidobacterium* species may be selected from *B. animalis* subsp *lactis*, *B. bifidum* and *B. infantis*; and the *Streptococcus* species may be *S. thermophilus*.

The method may comprise administration of a multi-strain probiotic combination. In an exemplary embodiment the multi-strain combination comprises *Lactobacillus rhamnosus*, *Streptococcus thermophilus*, *Bifidobacterium animalis* subsp. *lactis* and *Bifidobacterium bifidum*. In a further exemplary embodiment the multi-strain combination comprises *Lactobacillus bulgaricus*, *Lactobacillus paracasei*, *Lactobcillus gasseri*, *Lactobacillus rhamnosus*, *Lactococcus lactis*, *Bifidobacterium animalis* subsp. *lactis*, *Bifidobacterium infantis* and *Streptococcus thermophilus*. In a further exemplary embodiment, the multi-strain combination comprises *Lactobacillus acidophilus*, *Bifidobacterium bifidum* and *Streptococcus thermophilus*.

The SAMe may be present as a salt. The SAMe salt may be selected from, for example, SAMe tosylate, SAMe disulfate tosylate, SAMe disulfate monotosylate and SAMe butane disulfonate.

The method may further comprise the administration of one or more prebiotic components.

The depressive disorder may be major depressive disorder, dysthymic disorder, seasonal affective disorder, mood disorder, mixed anxiety-depressive disorder or bipolar disorder. The depression may be mild depression, moderate depression, severe depression or postpartum depression. The anxiety-related disorder may be generalised anxiety disorder, mixed anxiety-depressive disorder or post traumatic stress disorder.

The method may be employed as an adjunct to one or more other treatments or therapies for depression, anxiety or depressive or anxiety-related disorders.

The subject may suffer from treatment-resistant depression, anxiety or a depressive or anxiety-related disorder.

The subject may be a non-responder or a suboptimal responder for SAMe treatment of the depression, anxiety or a depressive or anxiety-related disorder, SSRI treatment of the depression, anxiety or a depressive or anxiety-related disorder, or SAMe+SSRI treatment of the depression, anxiety or a depressive or anxiety-related disorder.

In a second aspect the present disclosure provides a method for treating or ameliorating at least one symptom of treatment-resistant depression, comprising administering to a subject in need thereof an effective dose of orotic acid or a salt thereof.

By way of example only, the treatment-resistant depression may be depression that is resistant or non-responsive to one or more SSRIs and/or SAMe.

In a third aspect the present disclosure provides a composition for the treatment, prevention or amelioration of at least one symptom of depression, anxiety or a depressive or anxiety-related disorder, wherein the composition comprises orotic acid or a salt thereof in combination with one or more of the following:

(i) one or more probiotic microorganisms;
(ii) coenzyme Q10 (optionally a reduced or oxidized form thereof); and/or
(iii) SAMe or a salt thereof.

The exemplary embodiments the composition is in a form suitable for oral delivery. The composition may be in the form of a beverage, food, or beverage or food supplement. The composition may be in unit dosage form. In one embodiment, the unit dosage form is a capsule.

The orotic acid salt may comprise, for example, one or more of magnesium orotate, creatinine orotate, sodium orotate, calcium orotate, zinc orotate, chromium orotate, potassium orotate, copper orotate, iron orotate, manganese orotate, or choline orotate. In an exemplary embodiment the orotic acid salt is magnesium orotate or creatinine orotate. In specific embodiments of the present disclosure the orotic acid salt is not lithium orotate.

The one or more probiotic microorganisms may comprise at least one *Lactobacillus* species, at least one *Lactococcus* species, at least one *Bifidobacterium* species, at least one *Streptococcus* species and/or at least one yeast.

The one or more probiotic microorganisms may be selected from, for example, *Lactobacillus rhamnosus*, *Lactobacillus plantarum*, *Lactobacillus bulgaricus*, *Lactobacillus gasseri*, *Lactobacillus reuteri*, *Lactobacillus paracasei*, *Lactobacillus casei*, *Lactobacillus acidophilus*, *Lactobacillus fermentum*, *Lactobacillus salvarius*, *Lactococcus lactis*, *Streptococcus thermophilus*, *Bifidobacterium breve*, *Bifidobacterium bifidum*, *Bifidobacterium animalis* subsp. *lactis*, *Bifidobacterium animalis* subsp. *animalis*, *Bifidobacterium infantis*, *Bifidobacterium longum*, *Bifidobacterium pseudocatenulatum*, *Saccharomyces boulardii* or *Saccharomyces cerevisiae*.

In exemplary embodiments the *Lactobacillus* species may be selected from *L acidophilus*, *L. bulgaricus*, *L. paracasei*, *L. gasseri* and *L. rhamnosus*; the *Lactococcus* species may be *L. lactis*; the *Bifidobacterium* species may be selected from *B. animalis* subsp *lactis*, *B. bifidum* and *B. infantis*; and the *Streptococcus* species may be *S. thermophilus*.

The one or more probiotic microorganisms may be present as a multi-strain probiotic combination. In an exemplary embodiment the multi-strain combination comprises *Lactobacillus rhamnosus*, *Streptococcus thermophilus*, *Bifidobacterium animalis* subsp. *lactis* and *Bifidobacterium bifidum*. In a further exemplary embodiment the multi-strain combination comprises *Lactobacillus bulgaricus*, *Lactobacillus paracasei*, *Lactobcillus gasseri*, *Lactobacillus rhamnosus*, *Lactococcus lactis*, *Bifidobacterium animalis* subsp. *lactis*, *Bifidobacterium infantis* and *Streptococcus thermophilus*. In a further exemplary embodiment, the multi-strain combination comprises *Lactobacillus acidophilus*, *Bifidobacterium bifidum* and *Streptococcus thermophilus*.

The SAMe may be present as a salt. The SAMe salt may be selected from, for example, SAMe tosylate, SAMe disulfate tosylate, SAMe disulfate monotosylate and SAMe butane disulfonate.

The composition may further comprise one or more prebiotic components.

The composition may be administered as an adjunct to one or more other treatments or therapies for depression, anxiety or depressive or anxiety-related disorders.

In a fourth aspect the present disclosure provides a composition for the treatment, prevention or amelioration of at least one symptom of treatment-resistant depression, wherein the composition comprises orotic acid or a salt thereof in combination with one or more of the following:

(i) one or more probiotic microorganisms;
(ii) coenzyme Q10 (optionally a reduced or oxidized form thereof); and/or
(iii) SAMe or a salt thereof.

By way of example only, the treatment-resistant depression may be depression that is resistant or non-responsive to one or more SSRIs and/or SAMe.

In a fifth aspect the present disclosure provides the use of orotic acid or orotate as an active agent for the treatment, prevention or amelioration of at least one symptom of depression, anxiety or a depressive or anxiety-related disorder.

In a sixth aspect the present disclosure provides the use of orotic acid or a salt thereof in the manufacture of a medicament, food, beverage or supplement for the treatment, prevention or amelioration of at least one symptom of depression, anxiety or a depressive or anxiety-related disorder.

In a seventh aspect the present disclosure provides a method for treating, preventing or ameliorating at least one symptom of depression, anxiety or a depressive or anxiety-related disorder, comprising administering to a subject in need thereof an effective amount of one or more probiotic microorganisms selected from at least one *Lactobacillus* species, at least one *Lactococcus* species, at least one *Bifidobacterium* species, at least one *Streptococcus* species and/or at least one yeast.

The one or more probiotic microorganisms may be selected from, for example, *Lactobacillus rhamnosus, Lactobacillus plantarum, Lactobacillus bulgaricus, Lactobacillus gasseri, Lactobacillus reuteri, Lactobacillus paracasei, Lactobacillus casei, Lactobacillus acidophilus, Lactobacillus fermentum, Lactobacillus salvarius, Lactococcus lactis, Streptococcus thermophilus, Bifidobacterium breve, Bifidobacterium bifidum, Bifidobacterium animalis* subsp. *lactis, Bifidobacterium animalis* subsp. *animalis, Bifidobacterium infantis, Bifidobacterium longum, Bifidobacterium pseudocatenulatum, Saccharomyces boulardii* or *Saccharomyces cerevisiae*.

In exemplary embodiments the *Lactobacillus* species may be selected from *L. acidophilus, L. bulgaricus, L. paracasei, L. gasseri* and *L. rhamnosus*; the *Lactococcus* species may be *L. lactis*; the *Bifidobacterium* species may be selected from *B. animalis* subsp *lactis, B. bifidum* and *B. infantis*; and the *Streptococcus* species may be *S. thermophilus*.

The one or more probiotic microorganisms may be present as a multi-strain probiotic combination. In an exemplary embodiment the multi-strain combination comprises *Lactobacillus rhamnosus, Streptococcus thermophilus, Bifidobacterium animalis* subsp. *lactis* and *Bifidobacterium bifidum*. In a further exemplary embodiment the multi-strain combination comprises *Lactobacillus bulgaricus, Lactobacillus paracasei, Lactobcillus gasseri, Lactobacillus rhamnosus, Lactococcus lactis, Bifidobacterium animalis* subsp. *lactis, Bifidobacterium infantis* and *Streptococcus thermophilus*. In a further exemplary embodiment, the multi-strain combination comprises *Lactobacillus acidophilus, Bifidobacterium bifidum* and *Streptococcus thermophilus*.

The method may further comprises the administration of coenzyme Q10 (or a reduced or oxidised form thereof), SAMe or a salt thereof, and/or one or more prebiotic components.

The depressive disorder may be major depressive disorder, dysthymic disorder, seasonal affective disorder, mood disorder, mixed anxiety-depressive disorder or bipolar disorder. The depression may be mild depression, moderate depression, severe depression or postpartum depression. The anxiety-related disorder may be generalised anxiety disorder, mixed anxiety-depressive disorder or post traumatic stress disorder.

The method may be employed as an adjunct to one or more other treatments or therapies for depression, anxiety or depressive or anxiety-related disorders.

In an eighth aspect the present disclosure provides a composition for the treatment, prevention or amelioration of at least one symptom of depression, anxiety or a depressive or anxiety-related disorder, wherein the composition comprises one or more probiotic microorganisms selected from at least one *Lactobacillus* species, at least one *Lactococcus* species, at least one *Bifidobacterium* species, at least one *Streptococcus* species and/or at least one yeast.

The one or more probiotic microorganisms may be selected from, for example, *Lactobacillus rhamnosus, Lactobacillus plantarum, Lactobacillus bulgaricus, Lactobacillus gasseri, Lactobacillus reuteri, Lactobacillus paracasei, Lactobacillus casei, Lactobacillus acidophilus, Lactobacillus fermentum, Lactobacillus salvarius, Lactococcus lactis, Streptococcus thermophilus, Bifidobacterium breve, Bifidobacterium bifidum, Bifidobacterium animalis* subsp. *lactis, Bifidobacterium animalis* subsp. *animalis, Bifidobacterium infantis, Bifidobacterium longum, Bifidobacterium pseudocatenulatum, Saccharomyces boulardii* or *Saccharomyces cerevisiae*.

In exemplary embodiments the *Lactobacillus* species may be selected from *L. acidophilus, L. bulgaricus, L. paracasei, L. gasseri* and *L. rhamnosus*; the *Lactococcus* species may be *L. lactis*; the *Bifidobacterium* species may be selected from *B. animalis* subsp *lactis, B. bifidum* and *B. infantis*; and the *Streptococcus* species may be *S. thermophilus*.

The one or more probiotic microorganisms may be present as a multi-strain probiotic combination. In an exemplary embodiment the multi-strain combination comprises *Lactobacillus rhamnosus, Streptococcus thermophilus, Bifidobacterium animalis* subsp. *lactis* and *Bifidobacterium bifidum*. In a further exemplary embodiment the multi-strain combination comprises *Lactobacillus bulgaricus, Lactobacillus paracasei, Lactobcillus gasseri, Lactobacillus rhamnosus, Lactococcus lactis, Bifidobacterium animalis* subsp. *lactis, Bifidobacterium infantis* and *Streptococcus thermophilus*. In a further exemplary embodiment, the multi-strain combination comprises *Lactobacillus acidophilus, Bifidobacterium bifidum* and *Streptococcus thermophilus*.

In a ninth aspect the present disclosure provides the use of one or more probiotic microorganisms selected from at least one *Lactobacillus* species, at least one *Lactococcus* species, at least one *Bifidobacterium* species, at least one *Streptococcus* species and/or at least one yeast in the manufacture of a medicament, food, beverage or supplement for the treatment, prevention or amelioration of at least one symptom of depression, anxiety or a depressive or anxiety-related disorder.

BRIEF DESCRIPTION OF THE DRAWINGS

Embodiments of the present disclosure are described herein, by way of example only, with reference the following drawings.

FIG. 1 shows the response (OQ45 score) of subjects diagnosed with depression (n=8) to oral administration of 1600 mg magnesium orotate per day over an 8 week period.

DETAILED DESCRIPTION

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, typical methods and materials are described.

The articles "a" and "an" are used herein to refer to one or to more than one (i.e., to at least one) of the grammatical object of the article. By way of example, "an element" means one element or more than one element.

In the context of this specification, the term "about," is understood to refer to a range of numbers that a person of skill in the art would consider equivalent to the recited value in the context of achieving the same function or result.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

In the context of this specification, the term "probiotic" is to be given its broadest construction and is understood to refer to a microbial cell population or preparation, or component of a microbial cell population or preparation, which when administered to a subject in an effective amount promotes a health benefit in the subject.

In the context of this specification, the term "prebiotic" is to be given its broadest construction and is understood to refer to any non-digestible substance that stimulates the growth and/or activity of bacteria in the digestive system.

In the context of this specification, the terms "food", "foods", "beverage" or "beverages" include but are not limited to health foods and beverages, functional foods and beverages, and foods and beverages for specified health use. When such foods or beverages of the present invention are used for subjects other than humans, the terms can be used to include a feedstuff.

The term "subject" as used herein refers to any mammal, including, but not limited to, livestock and other farm animals (such as cattle, goats, sheep, horses, pigs and chickens), performance animals (such as racehorses), companion animals (such as cats and dogs), laboratory test animals and humans. Typically the subject is a human.

As used herein, the term "effective amount" refers to an amount of a composition that is sufficient to affect one or more beneficial or desired outcomes. An "effective amount" can be provided in one or more administrations. The exact amount required will vary depending on factors such as the identity and number of individual probiotic strains employed in the composition, the identity and number of compounds or agents employed in the composition, the subject being treated, the nature of any disease or condition suffered by the subject and the age and general health of the subject, and the form in which the composition is administered. Thus, it is not possible to specify an exact "effective amount". However, for any given case, an appropriate "effective amount" may be determined by one of ordinary skill in the art using only routine experimentation.

As used herein the terms "treating", "treatment" and the like refer to any and all applications which remedy, or otherwise hinder, retard, or reverse the progression of, a disorder or at least one symptom of a disease, including reducing the severity of a disorder. Thus, treatment does not necessarily imply that a subject is treated until complete elimination of, or recovery from, a disorder. Similarly, the terms "preventing", "prevention" and the like refer to any and all applications that prevent the establishment of a disorder or otherwise delay or retard the onset of a disorder or a symptom thereof.

The term "optionally" is used herein to mean that the subsequently described feature may or may not be present or that the subsequently described event or circumstance may or may not occur. Hence the specification will be understood to include and encompass embodiments in which the feature is present and embodiments in which the feature is not present, and embodiments in which the event or circumstance occurs as well as embodiments in which it does not.

Provided herein are methods for treating, preventing or ameliorating at least one symptom of depression, anxiety or a depressive or anxiety-related disorder, comprising administering to a subject in need thereof an effective dose of orotic acid or a salt thereof.

Also provided are methods for treating or ameliorating at least one symptom of treatment-resistant depression, comprising administering to a subject in need thereof an effective dose of orotic acid or a salt thereof.

Without wishing to be bound by theory, the applicant suggests that absorption of the orotic acid or salt thereof may be facilitated, stimulated or increased in the presence of one or more suitable probiotic microorganisms.

Accordingly, methods described herein may further comprise the administration of at least one additional agent selected from: one or more probiotic microorganisms; coenzyme Q10; and/or SAMe or a salt thereof.

Also provided are compositions for the treatment, prevention or amelioration of at least one symptom of depression, anxiety or a depressive or anxiety-related disorder, comprising orotic acid or a salt thereof in combination with one or more: one or more probiotic microorganisms; coenzyme Q10 (or a reduced or oxidised form thereof); and/or SAMe or a salt thereof.

In the context of this specification "depression" means a clinical disorder that includes a predominantly sad or depressed mood and is accompanied by psychological and/or physical symptoms, optionally presenting as a depressive or anxiety-related disorder. The depression may be mild depression, moderate depression, severe depression, clinical depression or postpartum depression. Exemplary depressive and anxiety-related disorders include, but are not limited to, major depressive disorder, dysthymic disorder, seasonal affective disorder, mood disorder, mixed anxiety-depressive disorder, bipolar disorder, generalised anxiety disorder, and post traumatic stress disorder, each of which are contemplated to be treated using the methods and compositions described herein.

Reference to treating and preventing depression, anxiety or a depressive or anxiety-related disorder as used herein includes, inter alia, the inhibition or alleviation, at least in part, of one or more symptoms of the depression, depressive disorder, anxiety or anxiety-related disorder. By way of example, symptoms of depression, anxiety and related disorders that may be inhibited or alleviated include irritability, mood swings, depressed mood, disturbed sleep, listlessness, short term memory loss, anxiousness, restlessness, tension, poor self esteem, suicidal thoughts or suicidal tendencies. Further, "treating or preventing" includes preventing the development of depression, anxiety or a depressive or anxiety-related disorder in a subject that may be predisposed to such a condition or may display one or more symptoms of such a condition but has not yet been diagnosed with the condition. "Treating or preventing" also include preventing the onset of a depressive episode or anxiety episode in a subject.

By "treatment-resistant depression" as used herein is meant any form of depression or related disorder that in any one or more given individuals has not responded to at least one adequate trial with antidepressant therapy, or that responds to a lesser extent or displays a diminished or reduced response to said treatment when compared to depression or related disorder in a subject that displays no resistance to said treatment. Thus, "treatment-resistant depression" may indicate complete or partial resistance to treatment. In the context of the present specification an individual suffering from depression or a related disorder that does not respond to a particular treatment may be referred to a 'non-responder' with respect to that treatment, and an individual suffering from depression or a related disorder that does not respond fully to a particular treatment (i.e. shows some level of resistance to treatment such that response is diminished when compared to the response of an individual suffering from depression or a related disorder that does not display resistance to said treatment) may be referred to a 'suboptimal-responder' with respect to that treatment (displays 'suboptimal treatment response'). The depression suffered by the individual may be referred to as treatment-resistant depression with respect to that treatment.

Though depressive feelings are common, depression or a depressive disorder is typically diagnosed only when the symptoms reach a threshold and last at least two weeks. There exist a number of methods and techniques well known to those skilled in the art for diagnosing depression, anxiety and depressive or anxiety-related disorders, for assessing the status or severity of such conditions or symptoms thereof over time, and for monitoring the change in status or severity of such conditions or symptoms thereof over time, including in response to treatment or therapy.

Such methods and techniques for diagnosing, assessing and monitoring depression, anxiety and depressive or anxiety-related disorders may comprise clinician assessment, self-assessment or self-reporting questionnaires, and clinician-completed reports or questionnaires, in addition to biochemical measurements. A variety of clinical measures of symptoms and mood are well known to those skilled in the art. The present disclosure contemplates the use of any such method(s) or technique(s) in diagnosing depression, anxiety or a depressive or anxiety-related disorder and for assessing or monitoring such conditions as part of, for example, an initial determination of the suitability of an individual to be treated in accordance with the present disclosure or a determination of the efficacy of a treatment in accordance with the present disclosure in an individual.

Exemplary self-assessment or self-report questionnaires include, but are not limited to the Depression and Anxiety Stress Scale (DASS), the Outcome Quiestionnaire-45 (OQ45), Quality of Life in Depression Scale (QLDS, including a Quality of Life (QoL) score), the Beck Depression Inventory (BDI), the Warwick-Edinburgh Mental Well-Being Scale (WBS), the Mini International Neuropsychiatric Interview (MINI), the Structured Clinical Interview for DSM Disorders (SCID) and the Patient Health Questionnaire (PHQ, such as PHQ-9 and PHQ-2). Exemplary clinician-completed reports or questionnaires include, but are not limited to, the Hamilton Depression Rating Scale (HAM-D) and the Raskin Depression rating Scale. Biochemical measurements that may be employed include, but are not limited to, whole blood serotonin levels.

OQ45 is an important measure used for treatment response tracking in both the psychological and health research and practice, and has proved a high valid measurement system. OQ45 is a self-report symptom and distress inventory designed as an independent measure of symptom distress and functioning to assess the response to intervention at regular intervals such as on a weekly bases ($\alpha=0.93$, & $\kappa>0.83$). The OQ45 consists of 45 items with a five point scale. A high total score <80 indicates a high level of symptom distress (anxiety, depression, and somatic, work and social role problems). Lower scores indicate less severity of problems. Average community non-clinical scores cut off (CO) occur at about >63, and changes of 14 points in either direction are typically considered clinically significant change and are reliable.

BDI is a 21-item self-report inventory that is widely used to assess depression. It has high internal constancy and correlates highly with other self-report measures of depression ($\alpha=0.60-0.90$).

The DASS short form is a 21 item self-report scale designed to measure depression and anxiety and was used here as a secondary self-report assessment. The DASS has high internal consistency and yields meaningful discriminations in a variety of settings ($\alpha=0.88-0.96$).

WBS has 14 items and assesses feelings and thoughts associated with mood ($\alpha=0.91$) with higher scores indicate better mood. It has a different factor structure to the BDI and DASS and was used in this study as a measure of mood improvement.

QoL has 16 items and evaluates perceived satisfaction with life over a number of domains ($\alpha=0.85$). QoL typically provides an important evaluation of perception of life circumstances and stressors.

The SCID clinical interview has acceptable validity in diagnosing personality disorder $\kappa>0.75$.

Suitable salts of orotic acid for use in accordance with embodiments of the present disclosure include, but are not limited to magnesium orotate, carnitine orotate, creatinine orotate, zinc orotate, calcium orotate, chromium orotate, potassium orotate, copper orotate, iron orotate, manganese orotate, sodium orotate and choline orotate. Those skilled in the art will appreciate that other salts may also be employed and the scope of the present disclosure is not limited by reference to any particular salt. However in particular embodiments, lithium orotate is expressly excluded from the scope of the present disclosure.

Also provided herein is the use of orotic acid or orotate as a therapeutically active agent for use in the treatment, prevention or amelioration of at least one symptom of depression, anxiety or a depressive or anxiety-related disorder.

The effective amount of orotic acid or salt thereof for use in accordance with the present disclosure may range from about 200 mg to about 4000 mg per day for a human subject. In certain embodiments, about 200 mg to about 4000 mg of orotic acid or a salt thereof per day is useful, e.g., about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 3000 mg or about 4000 mg, per day. In certain embodiments, orotic acid or a salt thereof is provided in a range of between about 200 mg to about 4000 mg, between about 200 mg to about 2000 mg, between about 400 mg to about 2000 mg, between 400 mg to about 1600 mg, between about 500 mg to about 2000 mg, between about 600 mg to about 2000 mg, between about 700 mg to about 2000 mg, between about 800 mg to about 2000 mg, between about 400 mg to about 1600 mg, between about 600 to about 1600 mg, or between about 800 mg to about 1600 mg inclusive, per day. In certain embodiments, the orotic acid or a salt thereof is provided in a range of between about 400 mg to about 1600 mg per day. In certain embodiments, the amount of orotic acid or a salt thereof administered per day is about 400 mg, about 800 mg, about 1200 mg or about 1600 mg. The amount to be administered to subjects or to be included in compositions disclosed herein will depend on a variety of factors including the identity of the compound or agent employed, the nature and extent of any condition suffered by the subject, and the form in which a composition is administered. For any given case, appropriate amounts may be determined by one of ordinary skill in the art using only routine experimentation.

In exemplary embodiments the orotic acid or salt thereof is administered in the form of a capsule. For example, where the daily dose is 800 mg, two 400 mg capsules may be taken, optionally as one capsule twice a day. Where the daily does is 1600 mg, four 400 mg capsules may be taken, optionally as two capsules twice a day.

In exemplary embodiments the one or more probiotic microorganisms to be employed, either alone or in combination with the orotic acid or salt thereof, the SAMe or salt thereof, coenzyme Q10 (or a reduced or oxidised form thereof) and/or one or more prebiotic components may comprise at least one *Lactobacillus* species, at least one *Lactococcus* species, at least one *Bifidobacterium* species, at least one *Streptococcus* species and/or at least one yeast.

The *Lactobacillus* may be selected from, for example, *L. acidophilus*, *L. bulgaricus*, *L. paracasei*, *L. gasseri* and *L. rhamnosus*. The *Lactococcus* may be, for example, *L. lactis*. The *Bifidobacterium* may be, for example, *B. animalis* subsp *lactis*, *B. bifidum* and/or *B. infantis*. The *Streptococcus* may be, for example, *S. thermophiles*. The yeast strain may be, for example, *S. boulardii* or *S. cerevisiae*.

In particular embodiments the one or more probiotic microorganisms may be selected from *Lactobacillus rhamnosus*, *Lactobacillus plantarum*, *Lactobacillus bulgaricus*, *Lactobacillus gasseri*, *Lactobacillus reuteri*, *Lactobacillus paracasei*, *Lactobacillus casei*, *Lactobacillus acidophilus*, *Lactobacillus fermentum*, *Lactobacillus salvarius*, *Lactococcus lactis*, *Streptococcus thermophiles*, *Bifidobacterium breve*, *Bifidobacterium bifidum*, *Bifidobacterium animalis* subsp. *lactis*, *Bifidobacterium animalis* subsp. *animalis*, *Bifidobacterium infantis*, *Bifidobacterium longum* and *Bifidobacterium pseudocatenulatum*.

The one or more probiotic microorganisms may be used or be present as specially selected strains as a culture concentrate or as part of a multi-strain blend, optionally with a variety of excipients. Accordingly, novel probiotic compositions for treating and preventing depression, anxiety and depressive and anxiety-related disorders are provided herein. Compositions of the present disclosure typically comprise strains of two or more bacterial species selected from *Lactobacillus rhamnosus*, *Lactobacillus plantarum*, *Lactobacillus bulgaricus*, *Lactobacillus gasseri*, *Lactobacillus reuteri*, *Lactobacillus paracasei*, *Lactobacillus casei*, *Lactobacillus acidophilus*, *Lactobacillus fermentum*, *Lactobacillus salvarius*, *Lactococcus lactis*, *Streptococcus thermophilus*, *Bifidobacterium breve*, *Bifidobacterium bifidum*, *Bifidobacterium animalis* subsp. *lactis*, *Bifidobacterium animalis* subsp. *animalis*, *Bifidobacterium infantis*, *Bifidobacterium longum* and *Bifidobacterium pseudocatenulatum*. In exemplary embodiments multi-strain combination for use in accordance with the present disclosure may comprise one or more of *Lactobacillus bulgaricus*, *Lactobacillus paracasei*, *Lactococcus lactis*, *Bifidobacterium animalis* subsp. *lactis*, *Lactobcillus gasseri* and *Streptococcus. thermophilus*.

The amounts of individual microbial strains to be administered to subjects or to be included in compositions disclosed herein will depend on a variety of factors including the identity and number of individual strains employed, the nature and extent of any condition suffered by the subject, and the form in which a composition is administered. For any given case, appropriate amounts may be determined by one of ordinary skill in the art using only routine experimentation.

By way of example only, the amount of each microbial strain present in a daily dose of a composition disclosed herein may be from about $1\times10^2$ cfu to about $1\times10^{11}$ cfu, and may be about $1\times10^3$ cfu, about $2.5\times10^3$ cfu, about $5\times10^3$ cfu, about $7.5\times10^3$ cfu, $1\times10^4$ cfu, about $2.5\times10^4$ cfu, about $5\times10^4$ cfu, about $7.5\times10^4$ cfu, about $1\times10^5$ cfu, about $2.5\times10^5$ cfu, about $5\times10^5$ cfu, about $7.5\times10^5$ cfu, about $1\times10^6$ cfu, about $2.5\times10^6$ cfu, about $5\times10^6$ cfu, about $7.5\times10^6$ cfu, about $1\times10^7$ cfu, about $2.5\times10^7$ cfu, about $5\times10^7$ cfu, about $7.5\times10^7$ cfu, about $1\times10^8$ cfu, about $2.5\times10^8$ cfu, about $5\times10^8$ cfu, about $7.5\times10^8$ cfu, about $1\times10^9$ cfu, about $2.5\times10^9$ cfu, about $5\times10^9$ cfu, about $7.5\times10^9$ cfu, about $1\times10^{10}$ cfu, about $2.5\times10^{10}$ cfu, about $5\times10^{10}$ cfu, about $7.5\times10^{10}$ cfu, and about $1\times10^{11}$ cfu.

By way of example only, the amount of each microbial strain present in a single dosage form of a composition disclosed herein (e.g. per capsule) may be from about $1\times10^2$ cfu to about $1\times10^{11}$ cfu, and may be about $1\times10^3$ cfu, about $2.5\times10^3$ cfu, about $5\times10^3$ cfu, about $7.5\times10^3$ cfu, $1\times10^4$ cfu, about $2.5\times10^4$ cfu, about $5\times10^4$ cfu, about $7.5\times10^4$ cfu, about $1\times10^5$ cfu, about $2.5\times10^5$ cfu, about $5\times10^5$ cfu, about $7.5\times10^5$ cfu, about $1\times10^6$ cfu, about $2.5\times10^6$ cfu, about $5\times10^6$ cfu, about $7.5\times10^6$ cfu, about $1\times10^7$ cfu, about $2.5\times10^7$ cfu, about $5\times10^7$ cfu, about $7.5\times10^7$ cfu, about $1\times10^8$ cfu, about $2.5\times10^8$ cfu, about $5\times10^8$ cfu, about $7.5\times10^8$ cfu, about $1\times10^9$ cfu, about $2.5\times10^9$ cfu, about $5\times10^9$ cfu, about $7.5\times10^9$ cfu, about $1\times10^{10}$ cfu, about $2.5\times10^{10}$ cfu, about $5\times10^{10}$ cfu, about $7.5\times10^{10}$ cfu, and about $1\times10^{11}$ cfu.

By way of example only, the combined amount of probiotic microbial strains present in a daily dose of a composition disclosed herein may be from about $1\times10^2$ cfu to about $1\times10^{11}$ cfu, and may be about $1\times10^3$ cfu, about $2.5\times10^3$ cfu, about $5\times10^3$ cfu, about $7.5\times10^3$ cfu, $1\times10^4$ cfu, about $2.5\times10^4$ cfu, about $5\times10^4$ cfu, about $7.5\times10^4$ cfu, about $1\times10^5$ cfu, about $2.5\times10^5$ cfu, about $5\times10^5$ cfu, about $7.5\times10^5$ cfu, about $1\times10^6$ cfu, about $2.5\times10^6$ cfu, about $5\times10^6$ cfu, about $7.5\times10^6$ cfu, about $1\times10^7$ cfu, about $2.5\times10^7$ cfu, about $5\times10^7$ cfu, about $7.5\times10^7$ cfu, about $1\times10^8$ cfu, about $2.5\times10^8$ cfu, about $5\times10^8$ cfu, about $7.5\times10^8$ cfu, about $1\times10^9$ cfu, about $2.5\times10^9$ cfu, about $5\times10^9$ cfu, about $7.5\times10^9$ cfu, about $1\times10^{10}$ cfu, about $2.5\times10^{10}$ cfu, about $5\times10^{10}$ cfu, about $7.5\times10^{10}$ cfu, and about $1\times10^{11}$ cfu.

By way of example only, the combined amount of probiotic microbial strains present in a single dosage form of a composition disclosed herein (e.g. per capsule) may be from about $1\times10^2$ cfu to about $1\times10^{11}$ cfu, and may be about $1\times10^3$ cfu, about $2.5\times10^3$ cfu, about $5\times10^3$ cfu, about $7.5\times10^3$ cfu, $1\times10^4$ cfu, about $2.5\times10^4$ cfu, about $5\times10^4$ cfu, about $7.5\times10^4$ cfu, about $1\times10^5$ cfu, about $2.5\times10^5$ cfu, about $5\times10^5$ cfu, about $7.5\times10^5$ cfu, about $1\times10^6$ cfu, about $2.5\times10^6$ cfu, about $5\times10^6$ cfu, about $7.5\times10^6$ cfu, about $1\times10^7$ cfu, about $2.5\times10^7$ cfu, about $5\times10^7$ cfu, about $7.5\times10^7$ cfu, about $1\times10^8$ cfu, about $2.5\times10^8$ cfu, about $5\times10^8$ cfu, about $7.5\times10^8$ cfu, about $1\times10^9$ cfu, about $2.5\times10^9$ cfu, about $5\times10^9$ cfu, about $7.5\times10^9$ cfu, about $1\times10^{10}$ cfu, about $2.5\times10^{10}$ cfu, about $5\times10^{10}$ cfu, about $7.5\times10^{10}$ cfu, and about $1\times10^{11}$ cfu.

Also contemplated by the present disclosure are variants of the microbial strains described herein. As used herein, the term "variant" refers to both naturally occurring and specifically developed variants or mutants of the microbial strains disclosed and exemplified herein. Variants may or may not have the same identifying biological characteristics of the specific strains exemplified herein, provided they share similar advantageous properties in terms of their ability to be used as probiotic strains suitable for the treatment or prevention of pain. Illustrative examples of suitable methods for preparing variants of the microbial strains exemplified herein include, but are not limited to, culturing under selective growth conditions, gene integration techniques such as those mediated by insertional elements or transposons or by homologous recombination, other recombinant DNA techniques for modifying, inserting, deleting, activating or silencing genes, intraspecific protoplast fusion, mutagenesis by irradiation with ultraviolet light or X-rays, or by treatment with a chemical mutagen such as nitrosoguanidine, methylmethane sulfonate, nitrogen mustard and the like, and bacteriophage-mediated transduction. Suitable and applicable methods are well known in the art and are described, for example, in J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); and J. Sambrook, D. Russell, *Molecular Cloning: A Laboratory Manual*, 3rd ed., Cold Spring Harbor Laboratory Press, Cold Spring Harbor, N.Y. (2001), inter alia.

Also encompassed by the term "variant" as used herein are microbial strains phylogenetically closely related to strains disclosed herein and strains possessing substantial sequence identity with the strains disclosed herein at one or more phylogenetically informative markers such as rRNA genes, elongation and initiation factor genes, RNA polymerase subunit genes, DNA gyrase genes, heat shock protein genes and recA genes. For example, the 16S rRNA genes of a "variant" strain as contemplated herein may share about 85%, 86%, 87%, 88%, 89%, 90%, 91%, 92%, 93%, 94%, 95%, 96%, 97%, 98% or 99% sequence identity with a strain disclosed herein.

The bacterial strains to be employed in accordance with the present disclosure may be cultured according to any suitable method known to the skilled addressee and may be prepared for addition to a composition by, for example, freeze-drying, spray-drying or lyophilisation. Thus, in embodiments of the present disclosure the bacterial strains may be in a dried form (such as lyophilized or sporulated form) in a suitable carrier medium, for example a FOS medium or other soluble fibre, sugar, nutrient or base material for the composition, with which the bacterial strains can be presented in an orally administrable form. One or more of the strains may be encapsulated in, for example, a suitable polymeric matrix to improve long term stability and storage of the compositions. In one example, encapsulation may comprise alginate beads, although those skilled in the art will appreciate that any suitable encapsulation material or matrix may be used. Encapsulation may be achieved using methods and techniques known to those skilled in the art.

Suitable salts of SAMe for use in accordance with embodiments of the present disclosure include, but are not limited to, SAMe tosylate, SAMe disulfate tosylate, SAMe disulfate monotosylate and SAMe butane disulfonate. Those skilled in the art will appreciate that other salts may also be employed and the scope of the present disclosure is not limited by reference to any particular salt.

The effective amount of SAMe or salt thereof for use in accordance with the present disclosure may range from about 200 mg to about 4000 mg per day for a human subject. In certain embodiments, about 200 mg to about 4000 mg of SAMe or a salt thereof per day is useful, e.g., about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 3000 mg or about 4000 mg, per day. In certain embodiments, SAMe or a salt thereof is provided in a range of between about 200 mg to about 4000 mg, between about 200 mg to about 2000 mg, between about 400 mg to about 2000 mg, between about 400 mg to about 1000 mg, between about 500 mg to about 2000 mg, between about 600 mg to about 2000 mg, between about 700 mg to about 2000 mg, between about 800 mg to about 2000 mg, between about 800 mg to about 1600 mg, between about 800 to about 1500 mg, between about 800 mg to about 1400 mg, between about 800 mg to about 1300 mg, between about 800 mg to about 1200 mg, between about 800 mg to about 1100 mg, between about 800 mg to about 1000 mg, or between about 800 mg to about 900 mg, inclusive, per day. In certain embodiments, the SAMe or a salt thereof is provided in a range of between about 800 mg to about 1600 mg per day. In certain embodiments, the amount of SAMe or a salt thereof administered per day is about 800 mg, about 1200 mg or about 1600 mg. The amount to be administered to subjects or to be included in compositions disclosed herein will depend on a variety of factors including the identity of the compound or agent employed, the nature and extent of any condition suffered by the subject, and the form in which a composition is administered. For any given case, appropriate amounts may be determined by one of ordinary skill in the art using only routine experimentation.

In some embodiments of the present disclosure as described herein coenzyme Q10 (CoQ10) is employed. The CoQ10 may be used in oxidised or recued form. The oxidised form may be, for example, ubiquinone. The reduced form may be, for example, ubiquinol. Those skilled in the art will appreciate that additional forms of CoQ10, and other examples of oxidised and reduced CoQ10, may be employed without departing from the scope of this disclosure.

In some embodiments, methods of the present disclosure may comprise administration to the subject of one or more prebiotic components. Similarly, in some embodiments compositions, in particular those comprising one or more probiotic microorganisms, may further comprise at least one prebiotic component. Suitable prebiotics include polydextrose, inulin, fructooligosaccharides (FOS), xylooligosaccharides (XOS), galactooligosaccharides (GOS), mannan oligosaccharides, protein-based green lipped mussel extract, and various prebiotic-containing foods such as raw onion, raw leek, raw chickory root and raw artichoke. In certain embodiments the prebiotic is a fructooligosaccharide. Those skilled in the art will appreciate that other sources of fibre and/or prebiotics may be added to the compositions.

In accordance with particular embodiments of the invention the at least one prebiotic component may be administered or be present in a composition in an amount of from about 1 mg to about 100 g, or more typically between about 5 mg to about 50 g. Alternatively, the composition may comprise about 10 mg, 100 mg, 1 g, 5 g, 10 g, 15 g, 20 g, 25 g, 30 g, 35 g, 40 g or 45 g of prebiotic.

In accordance with methods disclosed herein the various agents to be administered to a subject (including the orotic acid or salt thereof, the one or more probiotic microorganisms, the SAMe or salt thereof, the coenzyme Q10 (or a reduced or oxidised form thereof) and the one or more prebiotic components) may be coadministered sequentially or simultaneously, and may be administered as part of the same or different compositions or formulations. Moreover these agents may be coadministered with one or more other treatments or therapies for the treatment, prevention or amelioration of at least one symptom of depression, anxiety and depressive and anxiety-related disorders. By "coadministered" is meant simultaneous administration in the same composition or formulation or in two different compositions or formulations via the same or different routes or sequential administration by the same or different routes. By "sequential" administration is meant a time difference of from seconds, minutes, hours or days between the administration of the agents, compositions or treatments. Sequential administration may be in any order. For combination treatment containing multiple compositions or formulations, those skilled in the art will appreciate that composition or formulation forms (e.g. unit dosage forms) comprising the different agents or components to be administered need not be of the same type.

The compositions disclosed herein may further comprise vitamins and/or minerals and/or amino acids. The vitamins and minerals may be selected from, but not limited to: vitamins A, $B_1$, $B_2$, $B_3$, $B_5$, $B_6$, $B_9$, $B_{12}$, C, D, E and calcium, chromium, copper, fluorine, iodine, iron, magnesium, manganese, molybdenum, phosphorus, potassium, selenium, sodium and zinc. The amino acids may be selected from, but are not limited to: alanine, arginine, aspartic acid, cystine, glycine, histidine, lysine, methionine, phenylalanine, proline, serine, threonine, tryptophan and tyrosine.

Compositions of the present disclosure may be formulated for administration by any suitable route, such as oral or nasal administration or by inhalation. For these purposes a composition may be formulated by means known in the art into the form of for example, tablets, capsules, aqueous or oily solutions, suspensions, emulsions, nasal sprays, or finely divided powders or aerosols for inhalation.

Compositions may be prepared according to conventional methods well known in the pharmaceutical and nutriceutical industries, such as those described in Remington's Pharmaceutical Handbook (Mack Publishing Co., NY, USA) using suitable excipients, diluents and fillers. Exemplary additional ingredients include citric acid, magnesium oxide, silicon dioxide, etc. In general, oral compositions are prepared by uniformly and intimately bringing into association the components of the composition with a liquid carrier or finely divided solid carrier, or both and then, if necessary, shaping the product into the desired composition. Oral dosage forms may include soluble sachets, orally soluble forms, capsules, tablets, chewable tablets, multi-layer tablets with, for example, time- and/or pH-dependent release, and granulates.

Compositions suitable for oral administration may be presented as discrete units (i.e. dosage forms) such as gelatine or HPMC capsules, cachets or tablets, each containing a predetermined amount of each component of the composition as a powder, granules, as a solution or a suspension in an aqueous liquid or a non-aqueous liquid, or as an oil-in-water liquid emulsion or a water-in-oil liquid emulsion.

When the composition is formulated as capsules, the components of the composition may be formulated with one or more pharmaceutically acceptable carriers such as starch, lactose, microcrystalline cellulose and/or silicon dioxide. Additional ingredients may include lubricants such as magnesium stearate and/or calcium stearate. The capsules may optionally be coated, for example, with a film coating or an enteric coating and/or may be formulated so as to provide slow or controlled release of the composition therein.

Tablets may be prepared by compression or moulding, optionally with one or more accessory ingredients. Compressed tablets may be prepared by compressing in a suitable machine the components of the composition in a free-flowing form such as a powder or granules, optionally mixed with a binder, lubricant (for example magnesium stearate or calcium stearate), inert diluent or a surface active/dispersing agent. Moulded tablets may be made by moulding a mixture of the powdered composition moistened with an inert liquid diluent, in a suitable machine. The tablets may optionally be coated, for example, with a film coating or an enteric coating and/or may be formulated so as to provide slow or controlled release of the composition therein.

The compositions may be provided to the user in a powder form. The compositions may be added in powder form by the user to any type of drink or food product (for example water, fruit juice or yoghurt) and consumed thereafter. In another embodiment, the compositions may simply be consumed as a powder in the absence of a drink or additional food product.

The compositions may therefore be conveniently incorporated in a variety of food and/or beverage products, nutriceutical products, probiotic supplements, food additives, pharmaceuticals and over-the-counter formulations. The food or food additive may be a solid form such as a powder, or a liquid form. Specific examples of the types of beverages or foods include, but are not limited to water-based, milk-based, yoghurt-based, other dairy-based, milk-substitute based such as soy milk or oat milk, or juice-based beverages, water, soft drinks, carbonated drinks, and nutritional beverages, (including a concentrated stock solution of a beverage and a dry powder for preparation of such a beverage); baked products such as crackers, breads, muffins, rolls, bagels, biscuits, cereals, bars such as muesli bars, health food bars and the like, dressings, sauces, custards, yoghurts, puddings, pre-packaged frozen meals, soups and confectioneries.

The compositions may additionally include any suitable additives, carriers, additional therapeutic agents, bioavailability enhancers, side-effect suppressing components, diluents, buffers, flavouring agents, binders, preservatives or other ingredients that are not detrimental to the efficacy of the composition. In some embodiments, the probiotic strains may comprise from about 50% to about 90% by weight of the composition, based on the total weight of the composition including a carrier medium, or from about 60% to about 80% by weight of the composition.

Compositions of the invention can be readily manufactured by those skilled in the art using known techniques and processes. For example, in the case of probiotic-containing compositions, the probiotic microorganisms can be seeded from standard stock into a reactor and grown in standardized media until a predetermined CFU/g concentration is reached. The bulk material can then be drained from the reactor and dried by spray drying, lyophilization, or flatbed oven drying. The dried bacterial material can then be blended with the carrier medium and the resulting mixture can be pressed into tablets, filled into foil pouches as a granular solid, or introduced into gelatin capsules as a particulate material.

Also contemplated herein are packages, wherein a package comprises two or more separate components to be administered to a subject present in two or more separate unit dosage forms, wherein the separate unit dosage forms are intended to be coadministered. The unit dosage forms may be, for example, capsules. In an exemplary embodiment, a package may comprise in one unit dosage for orotic acid or a salt thereof, and in another unit dosage form one ore more probiotic microorganisms. The orotic acid or salt thereof may be in a dosage form suitable for the administration of an effective daily dose of the orotic acid or salt (for example, between about 400 mg to about 1600 mg per day) and the one or more probiotic microorganisms may be in a dosage form suitable for the administration of a daily dose of, for example, about 2000 mg of a multi-strain combination (200 billion CFU bacteria), and optionally 3000 mg prebiotic (such as FOS). A package may contain blister packs of capsules, each blister pack providing one, two or more days supply. Those skilled in the art will also appreciate that unit dosage forms comprising the different agents or components to be administered need not be of the same type.

In accordance with the present disclosure, compositions will normally be administered so that a symptom-ameliorating effective daily dose is received by the subject. The daily dose may be given in divided doses as necessary, the precise amount of the compound or agent received and the route of administration depending on the weight, age and sex of the subject being treated and on the particular disease condition being treated according to principles known in the art. A typical dosage regime is once or twice daily.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present disclosure will now be described with reference to the following specific examples, which should not be construed as in any way limiting the scope of the invention.

EXAMPLES

The following examples are illustrative of the invention and should not be construed as limiting in any way the general nature of the disclosure of the description throughout this specification.

Example 1

Magnesium Orotate in the Treatment of Depression

A pilot study of 8 subjects diagnosed with depression that did not adequately respond to prior treatment was conducted to investigate the effect of administration of 1600 mg per day magnesium orotate on depression over the course of eight weeks. The study received ethical approval from the Medical Research Ethics Committee (MREC) University of Queensland, Australia, within the guidelines of the National Statement on Ethical Conduct in Human Research. All participants provided written informed consent for the study.

The subjects were selected for inclusion in the study as follows. At the completion of a 15 week study investigating SAMe treatment of depression, suboptimal treatment responders (n=8) were inducted into the present orotate study after a 2 week wash out period. Sub-optimal treatment responders were defined as those still experiencing clinical depression by the SAMe study endpoint, which consisted of six participants with major depression and two with moderate depression. The subjects comprised six females between 33 to 70 years of age (mean age of 53 years) and two males between 48-54 years of age (mean age of 51 years). The orotate study was conducted as a single group study for 8 weeks (mean time for SAMe responders) with a focus was on efficacy.

Inclusion criteria also required a primary diagnosis of major depression that has a verifiable history of being treatment resistant, current medication type being SSRIs (for standardisation purposes), and at least 18 years of age with no upper age limit. Participants were also asked not to take any nutritional supplements such as B group vitamins or other supplements that have antidepressant effects (a list was provided to participants). Participants were excluded if they were a current high suicide risk, did not have major depression as a primary diagnosis, or were currently experiencing psychosis or had a diagnosis of bi-polar disorder, or were heavy substance misusers.

The magnesium orotate was administered in capsule form, each capsule comprising 400 mg magnesium orotate. The daily dose of 1600 mg magnesium orotate was provided as two capsules taken in the morning and two capsules taken at night.

Depression was monitored in the treated subjects over the eight week course using a variety of well known methodologies: the Beck Depression Inventory (BDI); the Depression and Anxiety Stress Scale (DASS); Outcome Questionnaire-45 (OQ45); the Warwick-Edinburgh Mental Well-Being Scale (WBS); and a Quality of Life (QoL score).

The mean BDI score for the total group (n=8) at the beginning of the eight week study was 33.8. Total group BDI change scores, pre-versus post treatment, were subjected to a two-way analysis of variance. The main effect of BDI change was $F(1,9)=8.76$, $p=0.021$ indicating that symptom scores (M=19) as proportion of change and (M=14.1 for endpoint, SD=12) reduced significantly.

50% of the group was in clinical remission by the endpoint of the study, while 30% remained moderately depressed, 10% mildly depressed, and 10% did not experience any clinical change.

A summary of the mean pre- and post-treatment scores for each of the measures of depression assessed are shown in Table 1.

TABLE 1

| Variable | Pre-Treatment | | Post-Treatment | |
| --- | --- | --- | --- | --- |
| | Mean (M) | SD | Mean (M) | SD |
| BDI | 33.8 | 7.1 | 14.1 | 12 |
| DASS | 44.7 | 7.8 | 25.2 | 21 |
| OQ45 | 86.6 | 25 | 54.2 | 9.4 |
| WBS | 34.6 | 3.9 | 45.6 | 10.3 |
| QoL | 55.2 | 8.6 | 76.0 | 24.5 |

Mean DASS, OQ45, WBS and QoL post-treatment versus pre-treatment change scores were each subjected to a two way analysis of variance. The results for DASS, WBS and QoL are shown in Tables 2 to 4, respectively.

DASS pre and post change scores were subject to a two way analysis of variance. The main effect of DASS change was $F(1, 7)=6.3$, $p=<0.035$ indicating symptom scores (M=25.2, SD=21.1) reduced significantly in the total group condition.

WBS pre and post change scores were subject to a two way analysis of variance. The main effect of WBS change was $F(1,7)=6.8$, $p=0.035$ indicating mood scores (M=14.1, SD=12) significantly increased in the total group condition.

QOL pre and post change scores were subject to a two way analysis of variance. The main effect of QOL change was $F(1,7)=10$, $p=0.004$ indicating quality of life scores (M=76.0, SD=20) significantly increased in the total group condition.

OQ45 pre and post change scores were subject to a two way analysis of variance. The main effect of OQ45 change was $F(1,9)=124$, $p=<0.001$ indicating function distress scores (M=54.2, SD=26.7) significantly decreased in the total group condition. The ratio of variance accounted for by change across all measurement points was moderate (partial eta$^2$=0.75). The change in mean group OQ45 scores over the course of the eight week study are shown in FIG. 1.

TABLE 2

| | | | | 95% Confidence Interval of the Difference | | | | |
|---|---|---|---|---|---|---|---|---|
| | | Std. | Std. Error | | | | | *Sig. |
| | Mean | Deviation | Mean | Lower | Upper | t | df | (2-tailed) |
| DASS-DASS8 | 19.50000 | 20.67435 | 7.30949 | 2.21581 | 36.78419 | 2.668 | 7 | .032 |

*indicates significant difference from baseline scores with a P < 0.05

TABLE 3

| | | | | 95% Confidence Interval of the Difference | | | | |
|---|---|---|---|---|---|---|---|---|
| | | Std. | Std. Error | | | | | *Sig. |
| | Mean | Deviation | Mean | Lower | Upper | t | df | (2-tailed) |
| MWBS-WMBS8 | −11.00000 | 10.90216 | 3.85450 | −20.11444 | −1.88556 | −2.854 | 7 | .025 |

*indicates significant difference from baseline scores with a P < 0.05

TABLE 4

| | | | | 95% Confidence Interval of the Difference | | | | |
|---|---|---|---|---|---|---|---|---|
| | | Std. | Std. Error | | | | | *Sig. |
| | Mean | Deviation | Mean | Lower | Upper | t | df | (2-tailed) |
| QoL-QoL8 | −20.75000 | 21.02210 | 7.43243 | −38.32491 | −3.17509 | −2.792 | 7 | .027 |

*indicates significant difference from baseline scores with a P < 0.05

Example 2

Magnesium Orotate and Probiotics in the Treatment of Depression

Three subjects were administered a probiotic supplement containing magnesium orotate for eight weeks, and measures of depression (BDI and OQ45) assessed. The subjects were selected for inclusion in the study as described in Example 1. The same inclusion and exclusion criteria were used. The subjects were female, of ages 35, 43 and 56.

The probiotic supplement administered comprised *Lactobacillus acidophilus*, *Bifidobacterium bifidum* and *Streptococcus thermophilus*, at a combined amount of about 10 billion CFU per two capsules. Each capsule of the supplement also included 400 mg magnesium orotate and 37.5 mg Coenzyme Q10. The supplement was administered in capsule form at 1600 mg/day, provided as two capsules taken in the morning and two capsules taken at night.

BDI and OQ45 were assessed for each subject as described in Example 1, at the beginning of the study prior to the initiation of treatment and again at the completion of eight weeks of combined magnesium orotate plus probiotic administration. The results are shown in Table 5. As can be seen, a substantial reduction in BDI and OQ45 was observed upon 8 weeks of treatment with the combined administration of probiotic supplement and magnesium orotate. A further five subjects have begun treatment with the combination of probiotic supplement and magnesium orotate as described above, with BDIs at intake (0 weeks) ranging from 30 to 39 and OQ45s at 0 weeks ranging from 89 to 121 (i.e. both consistent with the 0 week BDIs and OQ45s for the initial three subjects as shown in Table 5.

TABLE 5

| | BDI | | OQ45 | |
|---|---|---|---|---|
| Subject | 0 weeks | 8 weeks | 0 weeks | 8 weeks |
| 1 | 27 | 11 | 89 | 54 |
| 2 | 34 | 5 | 85 | 61 |
| 3 | 34 | 9 | 117 | 69 |

Example 3

Exemplary Probiotic-Containing Compositions

An exemplary probiotic-containing composition according to the present disclosure comprises *Lactobacillus acidophilus*, *Bifidobacterium bifidum* and *Streptococcus thermophilus*. The composition may comprise 5 billion CFU *L. acidophilus*, *B. bifidum* and *S. thermophilus* (combined). The composition optionally comprises 400 mg magnesium orotate.

Another exemplary probiotic-containing composition according to the present disclosure has the following ingredients:
Probiotic Components:
*L. rhamnosus*
*S. thermophilus*
*B. animalis* subsp. *lactis*,
*B. bifidum*
Combined preparation of the above strains at a concentration of about 50–100×10$^9$ CFU per dosage form (e.g. per capsule)
The composition optionally comprises 400 mg magnesium orotate. The composition optionally comprises coenzyme Q10, or a reduced or oxidised form thereof.
Optional Carrier Components:
magnesium oxide
magnesium gluconate
glutathione
FOS
Fructose
Optional Additional Excipients:
anhydrous citric acid
flavouring
colouring A further exemplary probiotic-containing composition according to the present disclosure has the following ingredients:
Probiotic Components:
*L. bulgaricus*,
*L. paracasei*,
*L. gasseri*,
*L. rhamnosus*
*Lactococcus Lactis* Subsp *lactis* [also known as *Streptococcus lactis*]
*B. animalis* subsp. *lactis*,
*B. infantis*
*S. thermophilus*
Combined preparation of the above strains at a concentration of at least 10$^9$ CFU per dosage form (e.g per capsule).
The composition optionally comprises 400 mg magnesium orotate. The composition optionally comprises coenzyme Q10, or a reduced or oxidised form thereof.
Optional Carrier Components:
*magnesium oxide*
*magnesium gluconate*
glutathione
FOS
Fructose
Optional Additional Excipients:
anhydrous citric acid
flavouring
colouring Products containing the above exemplary compositions, and any other compositions in accordance with the present disclosure may be formulated as a capsule, satchel, liquid, powder, gel or other delivery means.

Administration of said products may be one or two capsules twice a day.

The invention claimed is:

1. A method for treating, preventing or ameliorating at least one symptom of depression or a depressive disorder, comprising administering to a subject in need thereof an effective dose of orotic acid or a salt thereof, wherein the subject is a non-responder or suboptimal responder for S-adenosyl methionine (SAMe) treatment of the depression or depressive disorder, or is a non-responder or suboptimal responder for SAMe+selective serotonin reuptake inhibitor (SSRI) treatment of the depression or depressive disorder, and wherein the orotic acid salt comprises one or more of magnesium orotate, carnitine orotate, creatinine orotate, sodium orotate, calcium orotate, zinc orotate, chromium orotate, potassium orotate, copper orotate, iron orotate, manganese orotate, or choline orotate.

2. The method of claim 1, wherein the orotic acid salt comprises magnesium orotate or creatinine orotate.

3. The method of claim 1, wherein the orotic acid salt is not lithium orotate.

4. The method of claim 1, wherein the orotic acid salt comprises magnesium orotate and the effective dose of magnesium orotate is about 800 mg per day or more.

5. The method of claim 1, wherein the orotic acid salt comprises magnesium orotate and the effective dose of magnesium orotate is about 1600 mg per day.

6. The method of claim 1, wherein the orotic acid or salt thereof is administered orally.

7. The method of claim 6, wherein the orotic acid or salt thereof is in the form of a beverage, food, or beverage or food supplement.

8. The method of claim 1, wherein the orotic acid or salt thereof is administered in combination with at least one additional agent selected from:
  one or more probiotic microorganisms;
  coenzyme Q10 (optionally as a reduced or oxidized form); and/or
  SAMe or a salt thereof.

9. The method of claim 8, wherein the orotic acid or salt thereof and the at least one additional agent are administered as a single composition or formulation.

10. The method of claim 8, wherein the one or more probiotic microorganisms comprises a *Lactobacillus* species, a *Lactococcus* species, a *Bifidobacterium* species, a *Streptococcus* species and/or a yeast.

11. The method of claim 10, wherein the *Lactobacillus* species is selected from *L. bulgaricus*, *L. paracasei*, *L. gasseri* and *L. rhamnosus*; the *Lactococcus* species is *L. lactis*; the *Bifidobacterium* species is selected from *B. animalis* subsp *lactis*, *B. bifidum* and *B. infantis*; and the *Streptococcus* species is *S. thermophilus*.

12. The method of claim 8, wherein the one or more probiotic microorganisms are selected from *Lactobacillus rhamnosus, Lactobacillus plantarum, Lactobacillus bulgaricus, Lactobacillus gasseri, Lactobacillus reuteri, Lactobacillus paracasei, Lactobacillus casei, Lactobacillus acidophilus, Lactobacillus fermentum, Lactobacillus salvarius, Lactococcus lactis, Streptococcus thermophilus, Bifidobacterium breve, Bifidobacterium bifidum, Bifidobacterium animalis* subsp. *lactis, Bifidobacterium animalis* subsp. *animalis, Bifidobacterium infantis, Bifidobacterium longum, Bifidobacterium pseudocatenulatum, Saccharomyces boulardii* or *Saccharomyces cerevisiae*.

13. The method of claim 8, wherein the one or more probiotic microorganisms comprise *Lactobacillus rhamno-*

*sus, Streptococcus thermophilus, Bifidobacterium animalis* subsp. *lactis* and *Bifidobacterium bifidum.*

14. The method of claim 8, wherein the one or more probiotic microorganisms comprise *Lactobacillus bulgaricus, Lactobacillus paracasei, Lactobcillus gasseri, Lactobacillus rhamnosus, Lactococcus lactis, Bifidobacterium animalis* subsp. *lactis, Bifidobacterium infantis* and *Streptococcus thermophilus.*

15. The method of claim 8, wherein the SAMe is present as a salt, selected from SAMe tosylate, SAMe disulfate tosylate, SAMe disulfate monotosylate and SAMe butane disulfonate.

16. The method of claim 1, wherein the depressive disorder is major depressive disorder, dysthymic disorder, seasonal affective disorder, mood disorder, mixed anxiety-depressive disorder or bipolar disorder.

17. The method of claim 1, wherein the depression is mild depression, moderate depression, severe depression or postpartum depression.

18. The method of claim 1, wherein the method is employed as an adjunct to one or more other treatments or therapies for depression, anxiety or depressive or anxiety-related disorders.

\* \* \* \* \*